United States Patent [19]

O'Brien et al.

[11] Patent Number: 4,887,326
[45] Date of Patent: Dec. 19, 1989

[54] SUBOCCIPITAL PILLOW

[75] Inventors: Michael O'Brien, Boise; Lorie Leishman, Meridian; Christine A. O'Brien, Boise, all of Id.

[73] Assignee: Bax Associates, Boise, Id.

[21] Appl. No.: 247,533

[22] Filed: Sep. 22, 1988

[51] Int. Cl.⁴ .......................... A47G 9/00; A61F 7/00
[52] U.S. Cl. .......................................... 5/421; 5/441; 5/442; 5/490; 128/403
[58] Field of Search .................. 5/421, 434, 436, 441, 5/438, 442, 462, 485, 490; 128/403, 402, 380, 376, 377; 297/393; 62/261; D6/601

[56] References Cited

U.S. PATENT DOCUMENTS

| | | | |
|---|---|---|---|
| 1,542,561 | 6/1925 | Laskin et al. | 5/490 |
| 3,162,868 | 12/1964 | Cramer | 5/490 |
| 3,312,987 | 4/1967 | Emery | 5/441 |
| 3,780,537 | 12/1973 | Spencer | 128/403 |
| 3,840,918 | 10/1974 | Shave | 5/436 |
| 3,885,403 | 5/1975 | Spencer | 128/403 |
| 4,161,794 | 7/1979 | Darnfors | 5/441 |
| 4,204,543 | 5/1980 | Henderson | 128/403 |
| 4,676,247 | 6/1987 | Van Cleve | 128/403 |
| 4,783,866 | 11/1988 | Simmons et al. | 5/442 |

FOREIGN PATENT DOCUMENTS

| | | | |
|---|---|---|---|
| 838455 | 6/1960 | United Kingdom | 297/393 |
| 1048632 | 11/1966 | United Kingdom | 5/436 |

Primary Examiner—Alexander Grosz
Attorney, Agent, or Firm—Frank J. Dykas; Craig M. Korfanta

[57] ABSTRACT

A suboccipital pillow 10, for applying hot and/or cold treatments to the neck and suboccipital areas is provided, having a generally crescent shape, one side of which is fitted with a lightly insulated pocket 15a and the other side of which is fitted with a heavily insulated pocket 12a. Pillow 10 is filled with a soft cushion, such as a polyester fiber batting. Both pockets 12a and 15a have triangular tongues 16 and 17 attached to their open sides. Tongues 16 and 17 overlap and attach one to the other via a suitable fastener. A crescent shaped gel pack 21 is provided which may either be cooled in a refrigerator or freezer or heated in boiling water or in a microwave oven. After gel pack 21 has reached the desired temperature it is inserted in the appropriate pocket and the pocket is closed by overlapping and fastening the two tongues 16 and 17.

2 Claims, 3 Drawing Sheets

SUBOCCIPITAL PILLOW

BACKGROUND OF THE INVENTION

1. Technical Field

This invention generally relates to devices for applying therapeutic hot and cold treatments to the human body, and more particularly, it relates to a suboccipital pillow for applying hot and/or cold treatments to the suboccipital area of the neck and head.

2. Background Art

It is well known within the medical arts that the application of hot and/or cold treatments to portions of the body can alleviate substantial amounts of pain and discomfort, and further can aid in the healing process. Two particularly useful applications are those of treating stiff necks and migraine headaches. The difficulty in treating the neck and head area lies in keeping the hot or cold reservoir in contact with that portion of the body and at the same time keeping the patient comfortable.

A particularly useful device for applying either hot or cold treatments is taught by SPENCER, U.S. Pat. No. 3,780,537 and U.S. Pat. No. 3,885,403. Both patents teach a tough flexible envelope of plastic material within which is a gel which maintains a gel like consistency over a wide temperature range. The gel pack may be cooled within a freezer compartment or heated in boiling water, to a desired temperature for therapeutic use. While the gel pack of Spencer advantageously maintains its gel like consistency over a wide temperature range, it is not easily maintained juxtaposition the head and neck portions of the human body.

A device designed specifically for applying hot or cold treatments to the head area, is taught by SHAVE, U.S. Pat. No. 3,840,918. The device consists of a pillow having a flap provided with a pocket adapted to receive a temperature establishing means such as a heat pad or an ice pack. The pillow of Shave is particularly well adapted for applying treatment to either temple area. It is, however, not well adapted for applying hot or cold treatments to the suboccipital region of the head, as this would require the user to rest in the pillow face down, which is a particularly uncomfortable position for someone with a neck injury. Additionally, the pocket of Shave is not well adapted for use with a gel pack such as that taught by Spencer. When using a gel pack, it is advantageous to insulate the gel pack from the surrounding environment so as to limit the amount of heat absorption or loss and therefore prolong the treatment duration. This concern necessitates providing an insulated pocket wherein the side of the pocket adjacent the application area is insulated only to a point so as to prevent cold or heat damage to the skin, and the side of the pocket adjacent the environment is heavily insulated to prevent heat loss or absorption.

In practice, a gel pack is cooled within the freezer compartment of a household refrigerator, and hence, it is cooled to just below the freezing point of water, 32° F. The heat sink provided by gel pack cooled to this temperature, is normally insufficient to promote cold damage to the skin. It is therefore unnecessary to over insulate the side adjacent the treatment area of the gel pack containing pocket, and in fact, it is undesirable to do so, as doing so limits the rate of heat absorbtion from the treatment area. Heating a gel pack, on the other hand, is easily done in either a pan of boiling water or in a microwave oven. The resulting temperatures can very easily exceed the temperature at which skin burns. It is therefore desirable to heavily insulate the side adjacent the treatment area of the gel pack containing pocket so as to prevent burns. Therefore, for cooling purposes the treatment side of the pocket must be lightly insulated as opposed to being heavily insulated for use in heat treatment. The pillow of Shave provides only one pocket and is unsuitable for applying both hot and cold treatments using a gel pack.

DARNFORS, U.S. Pat. No. 4,161,794, teaches an inflatable cushion being shaped in a semi-toroidal fashion. The DARNFORS device is well suited for supporting the neck and suboccipital areas of the head of a patient while sitting. The device of DARNFORS, however, does not teach the use of either hot or cold treatments in connection therewith. This invention is designed for use by travelers to maintain there heads in a more comfortable upright position when the traveler is resting in a sitting position. Hence, the pillow is designed to have a uniform height or thickness all the way around it and is therefore not well suited for patients resting in a laying position.

What is needed is a device for simultaneously supporting the neck and suboccipital region of the head and applying hot and/or cold treatments thereto using convenient gel packs.

It is the object of the present invention to provide a supportive pillow which is capable of applying hot or cold treatments to the neck and suboccipital regions of the head which utilizes a gel pack for its heat sink or source. It is a further object of the present invention to provide a dual sized pillow wherein one side is particularly well suited for applying a heated gel pack while the other is well suited for applying a cooled gel pack.

DISCLOSURE OF INVENTION

These and other objects are accomplished by a suboccipital pillow having a generally crescent shape, one side of which is fitted with a lightly insulated pocket and the other side of which is fitted with a heavily insulated pocket. The pillow is filled with a soft cushion, such as a polyester fiber batting. Both pockets have triangular tongues attached to their open sides which overlap and attach one to the other via a suitable fastening means. A crescent shaped gel pack is provided which may either be cooled in a refrigerator or freezer or heated in boiling water or in a microwave oven. After the gel pack has reached the desired temperature it is inserted in the appropriate pocket and the pocket is closed by overlapping and fastening the two tongues together.

BEST MODE FOR CARRYING OUT INVENTION

Figure 1:
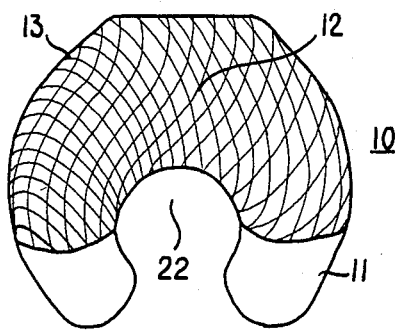
FIG. 1 is a plan view showing a first surface of a suboccipital pillow.
Figure 2:
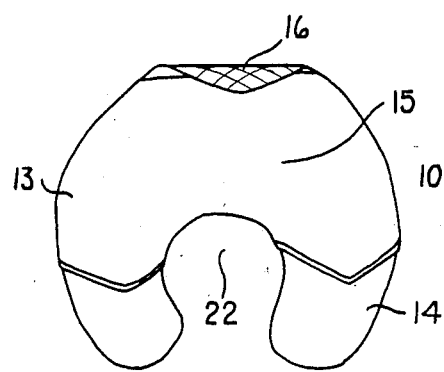
FIG. 2 is a plan view showing a second surface of a suboccipital pillow.

FIG. 1 shows a suboccipital pillow 10, which has a generally crescent shape. A first crescent shaped pocket panel 12 is attached to first surface 11, thereby defining pocket 12a, shown in FIG. 4, between pocket panel 12 and first surface 11. First surface 11 is further provided with quilted outer surface 13 which provides a heat insulator to prevent burning when placed next to the skin. FIG. 2 shows a second surface 14 having a second crescent shaped pocket panel 15 attached thereto, thereby defining a second pocket 15a, also shown in FIG. 4. The outer surface of pocket panel 15 is not necessarily insulated as pocket 15a is intended to contain a cooled gel packet. Suboccipital pillow 10 is generally constructed from a suitable textile and filled with a soft cushion such as a polyester fiber batting.

Figure 3:
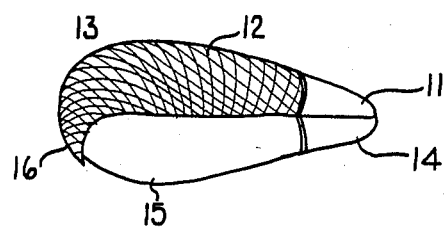
FIG. 3 is a side view of suboccipital pillow.

FIG. 3 shows the crescent shape of suboccipital pillow 10 to advantage. The pillow tapers downward from the back to the front, left to right in FIG. 3. The smaller front ends enable a person using the pillow to lay in a natural and comfortable position when using suboccipital pillow 10.

Figure 4:
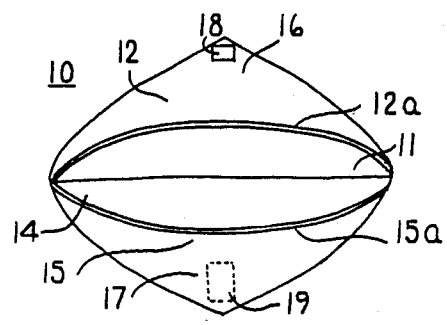
FIG. 4 is an end view showing the pocket tongues to advantage.

Referring also now to FIG. 4, suboccipital pillow 10 is shown in an end view with the pockets 12a and 15a open. Pocket panel 12, attached to the first side 11, has a triangular tongue 16 connected at its open edge while pocket panel 15, attached to surface 14, has a triangular tongue 17 connected to its open edge. Tongue 16 and 17 are designed to overlap, thereby closing both pockets. A suitable fastening means such as hook surface 18 and latch surface 19 is provided for fastening tongues 16 and 17 together. A suitable gel pack would be inserted in pocket 12a and/or pocket 15a.

Figure 5:
FIG. 5 is plan view of a standard gel pack.
Figure 6:
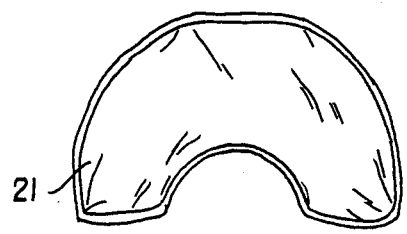
FIG. 6 is a plan view of a crescent shaped gel pack.

Referring also now to FIG. 5, a standard 5×10 gel pack 20 is shown. The suboccipital pillow 10 shown in FIGS. 1 through 4 is designed to accept a standard 5×10 gel pack 20. However, an improved crescent shaped gel pack 21 is provided and is shown in FIG. 6. Crescent shaped gel pack 21 provides additional heat sinking or sourcing capabilities and is better able to distribute the hot or cold treatment over a greater area of the neck and suboccipital regions of the head.

Figure 7:
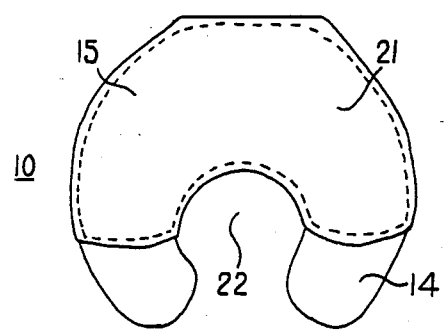
FIG. 7 is a plan view of a second surface of a suboccipital pillow having a crescent shaped gel pack inserted therein.

FIG. 7 shows suboccipital pillow 10 having a crescent shaped gel pack 21 inserted in pocket 15a.

To apply a cold treatment, the patient simply has to refrigerate gel pack 20 or 21 in a standard household refrigerator or freezer compartment and place the gel pack in pocket 15a. Pocket 15a is then closed by overlapping tongues 16 and 17 and fastening hook surface 18 and latch surface 19. The patient then inserts his or her neck into head/neck opening 22. The patient can comfortably sit or lay while applying the cold treatment. Heat treatments are applied in an analogous manner using a heated gel pack inserted in pocket 12a. Using a second gel pack, both hot and cold treatments can be applied simultaneously.

While there is shown and described the present preferred embodiment of the invention, it is to be distinctly understood that this invention is not limited thereto but may be variously embodied to practice within the scope of the following claims.

We claim:

1. A suboccipital pillow for administering hot and cold treatments to the suboccipital region of a head, comprising:
   a crescent shaped pillow having first and second surfaces;
   a first crescent shaped pocket panel attached to said first surface, thereby defining a first pocket and having an insulating outer surface for protecting a user from potential burns and for slowing the rate of heat loss or absorbtion of a gel pack contained in said first pocket;
   a second crescent shaped pocket panel attached to said second surface, thereby defining a second pocket;
   a first tongue attached to an open side of said first pocket panel;
   a second tongue attached to an open side of said second pocket panel;
   fastening means for closing said first and second pockets;
   a gel pack for insertion into either of said first or second pockets,
   one of said first and second tongues being adapted to overlap the other of said first and second tongues, and further being adapted to be releasably fastened thereto, thereby closing said first and second pockets.

2. The suboccipital pillow of claim 1 wherein said gel pack is crescent shaped to conform to the interior of either the first or second pockets.

* * * * *